United States Patent
Sharma et al.

(10) Patent No.: US 9,334,312 B2
(45) Date of Patent: May 10, 2016

(54) BIOLUBRICANT POLYPEPTIDES AND THERAPEUTIC USES THEREOF

(71) Applicants: Prashant Kumar Sharma, Groningen (NL); Andreas Herrmann, Groningen (NL); Anke Kolbe, Groningen (NL); Deepak Halenahally Veeregowda, Groningen (NL)

(72) Inventors: Prashant Kumar Sharma, Groningen (NL); Andreas Herrmann, Groningen (NL); Anke Kolbe, Groningen (NL); Deepak Halenahally Veeregowda, Groningen (NL)

(73) Assignees: RIJKSUNVIERSITEIT GRONINGEN, Groningen (NL); ACADEMISCH ZIEKENHUIS GRONINGEN, Groningen (NL)

( * ) Notice: Subject to any disclaimer, the term of this patent is extended or adjusted under 35 U.S.C. 154(b) by 215 days.

(21) Appl. No.: 14/046,350

(22) Filed: Oct. 4, 2013

(65) Prior Publication Data

US 2015/0098908 A1    Apr. 9, 2015

(51) Int. Cl.
*A61K 38/16* (2006.01)
*C07K 14/245* (2006.01)
*A61K 38/00* (2006.01)

(52) U.S. Cl.
CPC ............... *C07K 14/245* (2013.01); *A61K 38/00* (2013.01); *C07K 2319/21* (2013.01)

(58) Field of Classification Search
None
See application file for complete search history.

(56) References Cited

U.S. PATENT DOCUMENTS

| 5,900,405 | A * | 5/1999 | Urry ............................ 514/773 |
| 2002/0068304 | A1 * | 6/2002 | Urry ............................ 435/7.1 |
| 2004/0110439 | A1 * | 6/2004 | Chaikof et al. ............... 442/123 |
| 2005/0196440 | A1 | 9/2005 | Masters et al. |
| 2008/0226706 | A1 | 9/2008 | Kumar |

OTHER PUBLICATIONS

Won et al. A New Cloning Method for the Preparation of Long Repetitive Polypeptides without a Sequence Requirement. Macromolecules, 2002. vol. 35, pp. 8281-8287.*

Pesce et al. Enhancing cellular uptake of GFP via unfolded supercharged protein tags. Biomaterials, Jun. 2013. vol. 34, pp. 4360-4367.*

* cited by examiner

*Primary Examiner* — Marcela M Cordero Garcia
(74) *Attorney, Agent, or Firm* — Hoffmann & Baron, LLP

(57) ABSTRACT

The invention relates to the field of medicine. In particular, it relates to recombinant cationic polypeptides and their use as biolubricant. Provided is a biolubricant substance comprising the amino acid sequence $[(GKGVP)9]_n$, wherein n is ≥5.

Figure 1A:
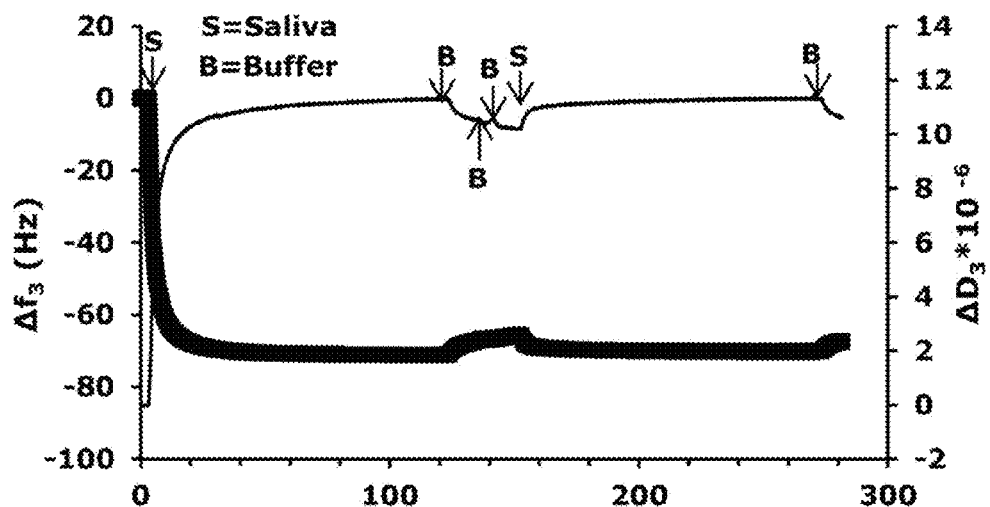
Figure 1B:
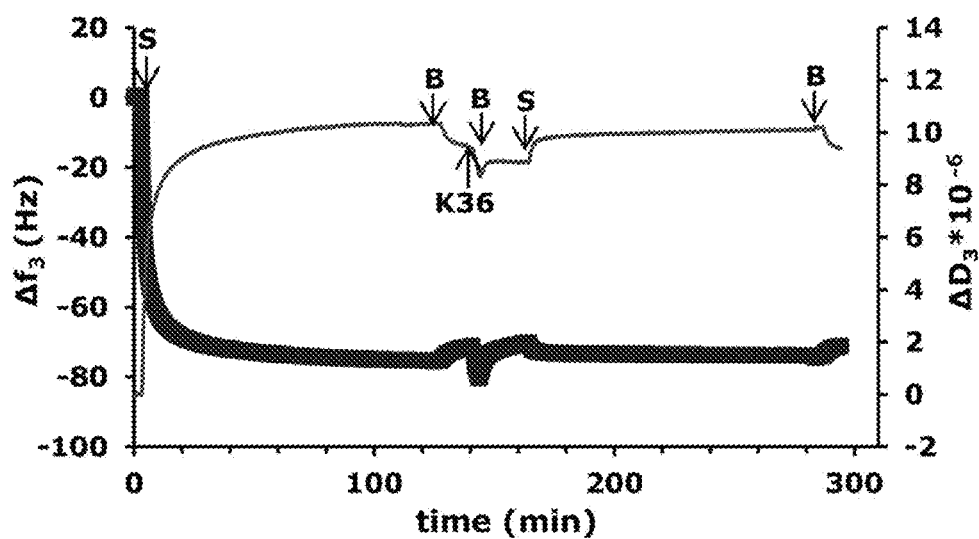
Figure 1C:
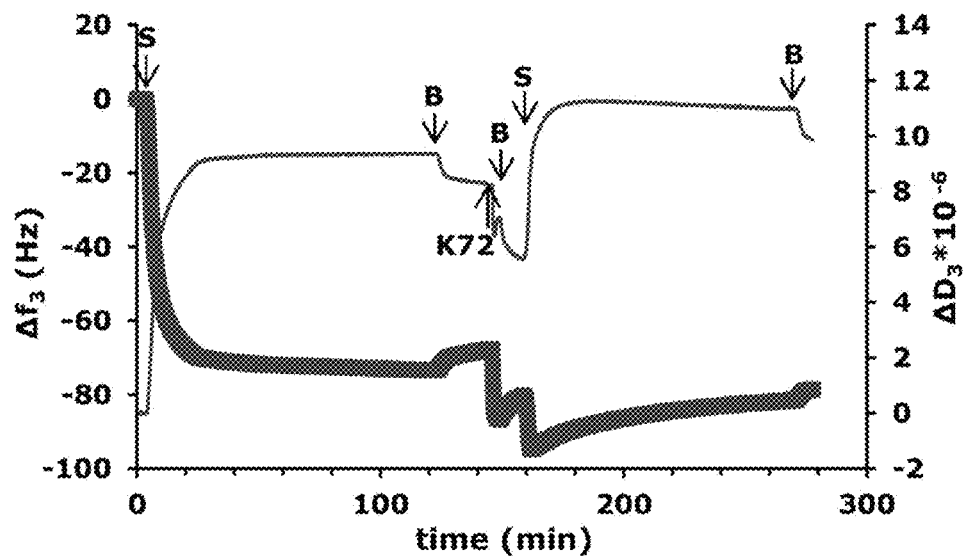

32 Claims, 8 Drawing Sheets renewed exposure of saliva "S-SCF with K36"

renewed exposure of saliva "S-SCF with K72"

BIOLUBRICANT POLYPEPTIDES AND THERAPEUTIC USES THEREOF

BACKGROUND OF THE INVENTION

The invention relates to the field of medicine. In particular, it relates to recombinant cationic polypeptides and their use as biolubricant, Biomacromolecules do not only fulfil complex functions inside the cell or within membranes, but proteinaceous materials may also play a very critical role at interfaces. One such example is biolubrication, where sliding surfaces coated with synthetic polymers and biological building blocks have been intensively investigated.[1] Biolubrication is an essential feature of health and can become impaired in the elderly or diseased.[2] Sjögren's syndrome, for instance, is a disease causing a variety of symptoms like dry eyes,[3] dry mouth,[4] vaginal dryness[5] and excessive friction and wear at the knee and hip joints.[6]

Biolubrication is mediated by glandular secretions containing (glyco-) proteins that adsorb at the sliding interface and form a conditioning film. Although water forms the basis of all biolubrication phenomena, it is easily removed from in between sliding surfaces during physiological activities associated with high contact pressures. To counter this, conditioning films providing biolubrication contain different glycoproteins that retain water molecules to generate repulsive hydration forces at the interface of the sliding surfaces.[7,8] Oral lubrication by adsorbed salivary conditioning films (SCFs)[9] is essential to facilitate speaking and mastication and protects against wear due to erosion[10] and abrasion.[11]

Maintenance of adequate biolubrication in the oral cavity is not only challenged by disease and aging, but also by high contact pressures. Contact pressures on molar surfaces during mastication can be as high as 86 MPa[12] which is one order of magnitude higher than the pressures experienced in hip and knee joints.[13] This load makes the maintenance and restoration of lubrication more challenging in the oral cavity than in other parts of the human body where articulating surfaces are involved.

Disorders associated with reduced or impaired biolubrication include xerostomia. Xerostomia refers to dry mouth caused by a lack of saliva and is often associated with some form of salivary gland dysfunction. In the field of oral care, xerostomia is problematic as saliva provides a protective effect on the teeth and can dilute or wash away harmful bacteria and/or food particles from the oral cavity. Failure to protect the teeth or allowing an accumulation of harmful bacteria/food particles can lead to bad breath (halitosis) or more seriously, to infections of the mucosal or periodontal tissue of the oral cavity.

Often, oral dryness is due to insufficient retention of water molecules in adsorbed SCFs due to low salivary flow rates (<1 mL min$^{-1}$) or dysfunction of a particular salivary gland.[2] Patients suffering from oral dryness symptoms are treated with artificial salivas, often containing lubricants like pig gastric mucins, polyacrylic acid and carboxymethyl cellulose.[14,15] However, artificial salivas only yield temporary relief in patients, as the adsorbed conditioning films are unable to sufficiently retain water due to lack of structural integrity.

Another disease associated with impaired biolubrication is dry eye syndrome or xerophthalmia. Xerophthalmia is a multifactorial disease of the tears and ocular surface that results in symptoms of discomfort, visual disturbance, and tears film instability with potential damage to the ocular surface. Multiple causes can lead to xerophthalmia, which is more common in elderly people. Amongst diseases causing xerophthalmia are found: vitamin A deficit, Sjögren syndrome, rheumatoid arthritis and other rheumatologic diseases, chemical or thermal burns, drugs such as atenolol, chlorpheniramine, hydrochlorothiazide, isotretinoin, ketorolac, ketotifen, levocabastin, levofloxacin, oxybutynin, tolterodine.

Recognizing the need for an improved approach to restore or enhance biolubrication, e.g. in the treatment of xerostomia or xerophthalmia, the present inventors set out to develop new biolubricants. In particular, they aimed at providing a biolubricant system that does not involve the administration of heterologous or artificial material e.g. in a bodily cavity, but which relies on strengthening the existing, though often impaired, endogenous conditioning film.

DESCRIPTION OF THE INVENTION

It was found that the above goals could be met by the provision of non-toxic, supercharged proteins having a specific cationic repeat unit of five amino acids, containing the aliphatic residues glycine (G), valine (V), proline (P) and positively charged lysine (K). Using salivary lubrication as test bed we show that these non-toxic, cationic, recombinant proteins with certain minimum positive charges works in concert with the existing lubrication system e.g. in the oral cavity. These proteins restore and enhance oral lubrication by first rigidifying the existing conditioning layer and then recruiting large glycoproteins (e.g. mucins) which help in lubrication and keeping the surfaces hydrated, thus decreasing the discomfort during speech, mastication and swallowing in addition to the general dry feeling. For the patients where the salivary glands are partly impaired the non-toxic, supercharged protein will strengthen the existing salivary conditioning film and cause preferential recruitment of mucins and improve the lubrication and hydration feeling in the mouth. For patients where the salivary glands are completely impaired, this protein along with heterologous mucins will do the job. This would improve the quality of patient life, who are suffering from either the Sjögren's syndrome or loss of salivary secretions due to radiation therapy around the Maxillofacial region.

Thus, not only can cationic supercharged, unfolded polypeptides (SUPs) of the invention interact with the negatively charged, naturally occurring mucins, they also possess significantly lower cytotoxicity than other cationic polyelectrolytes commonly used in biomedical applications. Moreover, they are well-defined with respect to their length, composition and charge density and are broken down into non-toxic, naturally occurring amino-acids upon digestion. Our strategy requires only small amounts of proteins which work in concert with the existing lubrication mechanism in the oral cavity. No existing commercial product uses this strategy.

Accordingly, the invention provides a proteinaceous biolubricant substance comprising the amino acid sequence [(GKGVP)(SEQ ID NO:1)$_9$]n wherein n is ≥5. In a related aspect, there is provided a substance comprising the general formula Head-[(GVGVP)(SEQ ID NO: 2)(GKGVP)(SEQ ID NO: 1)$_9$]n-Tail, wherein n is ≥5; Head is an amino acid sequence of at least 3 amino acids and Tail is an amino acid sequence of at least 3 amino acids, and the use thereof as biolubricant.

Biolubricant substances of the invention is herein also referred to as "supercharged, unfolded polypeptides", abbreviated as SUPs. A cationic SUP of the invention is characterized by a repeating amino acid sequence which is based on a motif found in elastin. Genetically engineered proteins comprising elastin-like blocks and their use as mucoadhesive are known in the art.

For example, US 2005/0196440 discloses various examples of repetitive amino acid sequences derived from, among others, elastin. Specifically disclosed is the elastin-like protein comprising the motif [(VPGVG)(SEQ ID NO: 4)$_4$]$_n$.

US2008/0226706 relates to personal care compositions comprising a bioactively effective amount of a repeat sequence protein polymer. Disclosed is a silk-elastin polymer SELP47K consisting exclusively of silk-like crystalline blocks and elastin-like flexible blocks. The silk repeating sequence units are used to impart durability and the elastin-like repeating sequence units are used to impart flexibility to the copolymer. SEQ ID NO:19 of US2008/0226706 contains 886 residues, among which the cationic sequence GKGVP (SEQ ID NO: 1). However, the remainder of the sequence consists of non-charged silk-like units having the sequence GAGAGS (SEQ ID NO: 7). As a result, a substance of US2008/0226706 has far less cationic charges than a supercharged substance of the invention, which is devoid of silk-like motifs and furthermore contains a high number of equidistant Lysine residues. This has the advantage of providing a highly charged peptide having a low charge density. The low charge density ensures that a SUP of the invention is non-toxic, and can thus be safely used in vivo.

As said, a biolubricant substance according to the invention is characterized by the presence of at least five repeated units having the sequence [(GKGVP)(SEQ ID NO: 1)$_9$]. This was found to have a clear effect on stiffening the basal SCF and decreasing the coefficient of fraction (COF).

Preferably however, the substance has an even higher cationic charge such that more negatively charged mucins can be absorbed. In one embodiment, the invention provides a biolubricant substance comprising the formula [(GKGVP)(SEQ ID NO: 1)$_9$]n, wherein n is ≥6, preferably ≥7, more preferably ≥8. For example, very good results were obtained with the SUP referred herein below to as "K72", comprising 72 charged lysines. The upper value of n is not critical to achieve the desired biolubricant effect. However, very large polypeptides are less preferred in view of their manufacture and/or purification. Typically, the value of n is up to 30, preferably up to 20. In one embodiment, n is an integer in the range of 5-20, like 6-18 or 8-14.

A biolubricant substance according to the invention can have a linear structure or a branched structure. Linear structures allow for the manufacture of a nucleic acid encoding the biolubricant polypeptide, and are therefore preferred in case the substance is prepared by recombinant expression. The biolubricant substance may, in addition to the cationic repeat sequence, comprise an N- and/or C-terminal extension. These may facilitate one or more steps during the (recombinant) manufacture of the substance e.g. cloning, expression, purification. In a specific embodiment, the cationic pentapeptide repeat sequence is preceded by the sequence GVGVP(SEQ ID NO: 2). Hence, the invention also relates to a biolubricant substance comprising the sequence [(GVGVP)(SEQ ID NO: 2)(GKGVP)(SEQ ID NO: 1)$_9$]$_n$ wherein n is ≥5, preferably ≥6, more preferably ≥7.

Still further, the repeat sequence is flanked by a Head and a Tail sequence, thus providing a biolubricant of the general formula Head-[(GVGVP)(SEQ ID NO: 2)(GKGVP)(SEQ ID NO: 1)$_9$]$_n$-Tail, wherein n is ≥5; Head is an amino acid sequence of at least 3 amino acids and Tail is an amino acid sequence of at least 3 amino acids.

The Head and Tail sequences of a biolubricant substance comprise at least 3 amino acids, preferably at least 4 amino acids. The upper limit is typically about 10-12 residues. The length of the Tail and Head can be the same or it can be different. In one embodiment, the Head sequence has a length of 3-5 amino acids. Preferred amino acids include non-charged amino acids, such as aliphatic residues like Gly, Val, Ala. Also preferred are Pro and Trp. In a specific aspect, the Tail sequence comprises about 3-6 amino acids selected from the group consisting of Gly, Ala, Val, Trp and Pro. For example, the Head sequence is GAGP (SEQ ID NO: 8). As another example, the Tail sequence is GGWP (SEQ ID NO: 9).

To facilitate isolation of a biolubricant substance, it may contain a protein tag sequence allowing for affinity purification of the substance. The tag sequence may be part of the Head or Tail sequence. Alternatively, it can be present within the supercharged "core" of the substance. Protein affinity tag sequences are known in the art.

A preferred protein tag is the polyhistidine-tag, which is an amino acid motif in proteins that consists of at least six histidine (His) residues, often at the N- or C-terminus of the protein. It is also known as hexa histidine-tag, 6×His-tag, and by the trademarked name His-tag. Polyhistidine-tags are often used for affinity purification of polyhistidine-tagged recombinant proteins expressed in *Escherichia coli* and other prokaryotic expression systems. Affinity purification using a polyhistidine-tag usually results in relatively pure protein when the recombinant protein is expressed in prokaryotic organisms. Bacterial cells are harvested via centrifugation and the resulting cell pellet lysed either by physical means or by means of detergents and enzymes such as lysozyme. At this stage raw lysate contains the recombinant protein among many other proteins originating from the bacterial host. This mixture is incubated with an affinity resin containing bound bivalent nickel or cobalt ions, which are available commercially in different varieties. Nickel and cobalt have similar properties and as they are adjacent period 4 transition metals ((v. iron triad)). These resins are generally sepharose/agarose functionalised with a chelator, such as iminodiacetic acid ($Ni^{2+}$-IDA) and nitrilotriacetic acid ($Ni^{2+}$-NTA) for nickel and carboxylmethylaspartate ($Co^{2+}$-CMA) for cobalt, which the polyhistidine-tag binds with micromolar affinity. The resin is then washed with phosphate buffer to remove proteins that do not specifically interact with the cobalt or nickel ion. Washing efficiency can be improved by the addition of 20 mM imidazole (proteins are usually eluted with 150-300 mM imidazole). Generally nickel-based resins have higher binding capacity, while cobalt-based resins offer the highest purity. The purity and amount of protein can be assessed by SDS-PAGE and Western blotting.

In one embodiment, the Tail or Head sequence of a biolubricant contains a polyhistidine tag. Preferably, the His-tag is located at the C- or N-terminus. For example, the Tail sequence is GGWPH$_6$ (SEQ ID NO: 10). As another example, the Head sequence is H$_6$GAGP (SEQ ID NO: 11). The skilled person will be able to design other variants of affinity-tag containing biolubricant peptides.

As said, a biolubricant substance according to the invention is suitably prepared by recombinant techniques using a suitable host cell that is provided with a nucleic acid encoding the substance. Hence, the invention also provides an isolated nucleic acid sequence encoding a (linear) polypeptide biolubricant substance of the invention. Also encompassed are expression vectors and other types of genetic carriers comprising an isolated nucleic acid of the invention. The nucleotide sequence encoding the biolubricant substance can be cloned preceded by regulatory sequences of expression and operatively bound to them. As used herein, the expression "operatively bound" means that the nucleotide sequences are within the adequate reading framework for expression under the control of these regulatory sequences.

Still further, the invention provides a host cell, preferably a bacterial host cell like *E. coli*, comprising an expression vector comprising a nucleic acid sequence encoding a biolubricant substance of the invention. Preferably, the host is a so-called 'GRAS' (generally recognized as safe) microorganism, such that the substance produced can be used for clinical applications.

In an alternative embodiment, the biolubricant peptide has a branched structure. Provided is a branched proteinaceous biolubricant substance having a degree n of branching, each of the branches comprising the amino acid sequence (GKGVP)(SEQ ID NO: 1)m wherein m times n is at least 40, preferably at least 45, more preferably at least 50. Branched SUPs can be prepared by chemical methods known in the art. See for example Kowalczyk et al., J. Pept. Sci. 2011; 17: 247-251. Typically, m is in the range of 2-10. Preferably, n is at least 5, more preferably at least 7, most preferably at least 10. For example, the substance comprises at least eight branches, each of which comprises at least one repeat of the cationic repeat sequence (GKGVP)(SEQ ID NO: 1)m, wherein 5≤m≤10. In a specific aspect, the substance is hyperbranched and has at least 10 branches. For example, the substance comprises at least 16 branches, each of which comprises at least one repeat of the cationic repeat sequence (GKGVP)(SEQ ID NO: 1)m, wherein 3≤m≤10. The skilled person will understand that numerous other branched variants can be made which satisfy the overall requirement that the biolubricant substance contains a total amount of at least 40 positively charged residues.

Also provided herein is a composition comprising a biolubricant substance according to the invention and a pharmaceutically acceptable carrier, diluent or excipient. The composition of the invention can contain an amount of biolubricant substance that can vary within a wide range, but always at therapeutically effective amounts.

In this invention a "therapeutically effective amount" is defined as the amount of a biolubricant sufficient to cause an increase in biolubrication of a bodily cavity, in particular in tearing, vaginal secretion or salivary secretion in a patient. Therefore, the composition of the invention can contain an amount of biolubricant substance ranging from 0.1 to 2,000 mg, preferably within the range from 0.5 to 500 mg and, even more preferably, from 1 to 200 mg. Appropriate doses of the compositions can range from 0.01 to 100 mg/kg of body weight, preferably from 0.1 to 50 mg/kg of body weight, more preferably, from 0.5 to 20 mg/kg of body weight. The composition can be administered a variable number of times a day, in particular from 1 to 4 four doses a day.

In one embodiment of the invention, the oral care composition of the invention is topically delivered to the oral cavity. In another embodiment of the invention the dry mouth alleviating component of the invention does not provide a systemic effect. The dosage regimen will be established by the physician and the clinical factors. As it is well known in medicine, the dosages depend on many factors, including the physical characteristics of the patient (age, size, sex), the administration route used, the severity of the disease, the particular compound used and the pharmacokinetic properties of the subject In one embodiment, the composition is an oral care composition that alleviates dry mouth comprising a biolubricant substance as disclosed herein, and optionally one or more further dry mouth alleviating component(s). For example, it allows for the treatment of patients undergoing radiotherapy-particularly to the mouth, oropharynx, or neck area, who may experience dry mouth that results from damage to the salivary glands.

The oral care composition comprises an orally acceptable vehicle. Any suitable orally acceptable vehicle can be used, such as those described in U.S. Pat. No. 4,894,220 titled "Antibacterial Anti-Plaque Oral Composition," which is incorporated by reference herein. For example, the vehicle can include a water-phase with humectant. In the present invention, the water and humectant liquid phase can comprise at least 10% by weight of the oral care composition. Moreover, preferably the humectant comprises propylene glycol, which can help to solubilize the biolubricant substance. The remainder of the humectant is preferably glycerine and/or sorbitol and/or xylitol. Water is present typically in amount of at least 3% by weight; and glycerine and/or sorbitol and/or xylitol typically total 6.5% to 75% by weight of the oral preparation, more typically 10% to 75%, and, together with the solubilizing humectant, the essential humectant components typically amount to 7% to 80% by weight of the oral preparation. Reference hereto to sorbitol refers to the material typically as available commercially in 70% aqueous solutions.

A humectant, such as glycerine, sorbitol, xylitol, propylene glycol, ethanol and mixtures thereof may be present in an amount of 10 to 30% by weight. The oral care composition may contain water at 5% to 30% by weight. Liquid dentifrices typically contain 50% to 85% of water, may contain 0.5% to 20% by weight of non-toxic alcohol and may also contain 10% to 40% by weight of humectant, such as glycerine, sorbitol, and/or xylitol. Sorbitol refers to the material typically available commercially in 70% aqueous solutions.

As another example, the composition is an ocular care or ophthalmic composition formulated for topical administration of a biolubricant substance of the invention to the eye. Such composition is suitably used for the treatment or prevention of dry eye syndrome. The normal tear film is a relatively stable, thin film composed of a superficial lipid layer and an aqueous layer intermixed with a mucus gel layer which is partially adherent to the corneal and conjunctival surface epithelium. Natural tear film is important for the lubrication and maintenance of the refractive surface of the eye. Dry eye syndrome is a complex disease characterized by a dysfunction of one or more components of the tear film, leading to the loss of tear film stability, a hyperosmotic shift in the tear film osmotic balance, and/or an inadequate amount of fluid on the ocular surface. This is characterized by rapid break-up of the tear film and numerous symptoms, including burning/stinging, foreign body sensation, itching, and photophobia.

Treatments used to treat xherophtalmia include corticosteroids which may be effective in early stages of the disease, vitamin A supplements and pilocarpine which is a drug that increases tear production. Among improve dryness preparations (artificial tears) solutions hypromellose and carbomer gels which are applied to the conjunctiva are used. However, these treatments have clear limitations regarding its efficacy and toxicity. Therefore, there is a need to provide new improved treatments for xherophtalmia.

It has now been discovered that a biolubricant substance of the invention is advantageously used in novel ophthalmic compositions for treating dry eye syndrome. Beneficial effects of biolubricant substance addition, preferably in an amount of at least 0.05% w/v, is envisaged both with traditional artificial tears simply containing saline or hypromellose and the newer hyaluronic acid based artificial tears. With traditional formulation the presence of biolubricant may cause recruitment of PRG4 molecules, giving rise to better lubrication. A formulations comprising a biolubricant as herein disclosed is not only expected to recruit PRG4 but also to lubricate the cornea-eyelid interface by synergistically interacting with hyaluronic acid, a well known mechanism in the field of cartilage lubrication. See Das et al. (Biomacromolecules, 2013, 14(5), 1669-1677).

Compositions may be used to treat dry eye, or to diagnose, cure, mitigate, treat, or prevent dry eye syndrome in man or other animals. The formulations are sterile, buffered, oil and water emulsion artificial tear products formulated for the relief of ocular surface irritation and symptoms of dryness. Also provided is a method of treating, diagnosing, curing, mitigating or preventing dry eye syndrome comprising administering an effective amount of an ophthalmic composition according to the invention to an eye of a man or other animal in need thereof.

An ocular care composition typically comprises ophthalmically acceptable liquids. An ophthalmically acceptable liquid includes a liquid formulated that is tolerable to a patient for topical ophthalmic use. Additionally, an ophthalmically acceptable liquid could either be packaged for single use, or for multiple uses containing a preservative to prevent contamination. For ophthalmic application, solutions or medicaments may be prepared using a physiological saline solution as a major vehicle. Ophthalmic solutions may be maintained at a comfortable pH with an appropriate buffer system. The formulations may also contain conventional, pharmaceutically acceptable preservatives, stabilizers and surfactants.

An ophthalmically acceptable liquid may include further demulcents or film forming materials. Examples of demulcents may include, but are not limited to polymers such as polyvinyl alcohol, povidone, hydroxypropyl methyl cellulose, poloxamers, carboxymethyl cellulose, hydroxyethyl cellulose, acrylates; surfactants such as polyoxyethylene (80) sorbitan monooleate and glycerin. The amount of demulcent may vary. In some embodiments, the amount of any demulcent such as those listed above may be from about 0.1% w/w to about 2% w/w, or from about 0.3% w/w to about 0.7% w/w, or from about 0.3% w/w to about 0.5% w/w, or about 0.5% w/w.

An ophthalmically acceptable liquid may include a buffer. The buffer may vary, and may include any weak conjugate acid-base pair suitable for maintaining a desirable pH range. Examples include, but are not limited to, acetate buffers, citrate buffers, phosphate buffers, borate buffers, or a combination thereof. Acids or bases may be used to adjust the pH of these formulations as needed. The amount of buffer used may vary. In some embodiments, the buffer may have a concentration in a range of about 1 nM to about 100 mM. The pH of a buffered solution may be increased by the addition of sodium hydroxide or another base, or decreased by the addition of hydrochloric acid or another acid. In some embodiments, the pH of a composition may be from about 7 to about 7.5, or from about 7.2 to about 7.4, or about 7.3.

An ophthalmically acceptable liquid may include a preservative. The preservative may vary, and may include any compound or substance suitable for preventing microbial contamination in an ophthalmic liquid subject to multiple uses from the same container. Preservatives that may be used in the pharmaceutical compositions disclosed herein include, but are not limited to, cationic preservatives such as quaternary ammonium compounds including benzalkonium chloride, polyquad, and the like; guanidine-based preservatives including polyhexamethylene biguanide (PHMB), chlorhexidine, and the like; chlorobutanol; mercury preservatives such as thimerosal, phenylmercuric acetate and phenylmercuric nitrate; and oxidizing preservatives such as stabilized oxychloro complexes (e.g. Purite®). Purite® is a registered trademark of Allergan, Inc. In some embodiments, the amount of preservative in the liquid may be from about 0.0001% w/w to about 25% w/w, or from about 0.002% w/w to about 0.05% w/w, or from about 0.005% w/w to about 0.02% w/w, or about 0.01% w/w.

An ophthalmically acceptable liquid may include a surfactant. The surfactant may vary, and may include any compound that is surface active or can form micelles. A surfactant may be used for assisting in dissolving an excipient or an active agent, dispersing a solid or liquid in a composition, enhancing wetting, modifying drop size, stabilizing an emulsion, or a number of other purposes. Useful surfactants include, but are not limited to, surfactants of the following classes: alcohols; amine oxides; block polymers; carboxylated alcohol or alkylphenol ethoxylates; carboxylic acids/fatty acids; ethoxylated alcohols; ethoxylated alkylphenols; ethoxylated arylphenols; ethoxylated fatty acids; ethoxylated fatty esters or oils (animal and vegetable); fatty esters; fatty acid methyl ester ethoxylates; glycerol esters; glycol esters; lanolin-based derivatives; lecithin and lecithin derivatives; lignin and lignin derivatives; methyl esters; monoglycerides and derivatives; polyethylene glycols; polymeric surfactants; propoxylated and ethoxylated fatty acids, alcohols, or alkyl phenols; protein-based surfactants; sarcosine derivatives; sorbitan derivatives; sucrose and glucose esters and derivatives. In some embodiments, the surfactant may include polyethylene glycol (15)-hydroxystearate (CAS Number 70142-34-6, available as Solutol HS 15® from BASF), polyoxyethylene-polyoxypropylene block copolymer (CAS No. 9003-11-6, available as Pluronic® F-68 from BASF), polyoxyethylene 40 stearate (POE40 stearate), polysorbate 80 or polyoxyethylene (80) sorbitan monooleate (CAS No. 9005-65-6), sorbitane monostearate (CAS No. 1338-41-6, available as Span™ 60 from Croda International PLC), polyoxyethylenglycerol-triricinoleat 35 (CAS No. 61791-12-6, available as Cremophor EL® from BASF). The amount of surfactant may vary. In some embodiments, the amount of any surfactant such as those listed above may be from about 0.001% w/w to about 5% w/w, or from about 0.1% w/w to about 2 w/w %, or from about 0.3% to about 0.7%, or from about 0.3% w/w to about 0.5% w/w, or from about 0.1% w/w to about 1% w/w, or about 0.5% w/w.

The invention also provides a method for treating or preventing a condition associated with impaired lubrication of a bodily cavity, comprising administering to a subject in need thereof a therapeutically effective amount of a biolubricant substance or a composition according to the invention. For example, the bodily cavity is the oral, ocular or vaginal cavity. Thus, in one embodiment the condition is selected from xerostomia, xerophthalmia, Atrophic Vaginitis (vaginal dryness) and Sjögren's syndrome. The subject is preferably a mammal, more preferably a human. The invention therefore also encompasses veterinary applications of a supercharged biolubricant substance.

LEGENDS TO THE FIGURES

FIG. 1. Influence of adsorption of recombinant cationic SUPs and renewed exposure to saliva on the softness of salivary conditioning films. (a, b, c) Examples of the QCM-D response as a function of time to protein adsorption from saliva on Au-coated quartz crystal surfaces, subsequent adsorption of cationic recombinant SUPs (2 min) and renewed exposure to salivary proteins, expressed as changes in third harmonic frequency ($\Delta f3$, thick line) and dissipation ($\Delta D3$, thin line), together with structural softness of the adsorbed films: a) buffer/no recombinant SUP adsorption; b) adsorption of recombinant K36 and c) adsorption of recombinant K72. (d) Structural softness of salivary conditioning films after buffer treatment or recombinant cationic SUP adsorption i. e. treated SCF and after renewed exposure to saliva i.e. secondary SCF (S-SCF). Error bars represent the standard deviation over five independent measurements. Statistically significant (p<0.05, two tailed Student t-test) differences in softness of films with adsorbed K36 or K72 with respect to control films are indicated by *. Significant differences in softness between films with adsorbed K72 and K36 are indicated by #.

FIG. 2. Influence of adsorption of recombinant cationic SUPs and renewed exposure to saliva on the friction forces, repulsive force upon approach and glycosylation of salivary conditioning films. (a, b) Friction force as a function of normal force during increasing (closed symbols) and decreasing (open symbols) normal forces: a) bare Au-coated QCM crystal and S-SCF without adsorbed recombinant cationic SUPs; b) S-SCFs with adsorbed recombinant cationic SUPs K36 or K72 and after renewed exposure to salivary proteins. Error bars represent standard deviations over 12 measurements. c) Example of the repulsive force as a function of tip separation distance for bare Au-coated QCM crystals, S-SCF without adsorbed recombinant cationic SUPs and with adsorbed K36 or K72. The repulsive force range (D) for all adsorbed protein films is calculated with respect to hard contact recorded on bare Au-coated crystal surface (inset FIG. 2c). Error bars represent standard deviations over 30 force curves. d) The degree of glycosylation (% Oglyco) for S-SCFs without adsorbed recombinant cationic SUPs and with adsorbed K36 or K72, obtained from a decomposition of the O1s photoelectron peak in XPS. Error bars represent the standard deviations over three independent XPS measurements on separately prepared samples. Statistically significant (p<0.05, two tailed Student t-test) differences in repulsive force range (c) and glycosylation (d) of S-SCF with K36 or K72 with respect to S-SCF in absence of adsorbed recombinant SUPs are indicated by *. Differences in repulsive force range between S-SCF with adsorbed K36 or K72 are indicated by #.

FIG. 3. Architecture of SCFs after adsorption of recombinant cationic SUPs with different numbers of positive charges and renewed exposure to saliva. a) Adsorbed salivary conditioning film, showing glycosylated mucins adsorbed in loops and trains over a layer of adsorbed densely packed low-molecular weight proteins, including proline-rich proteins, histatins and lysozymes. b) Salivary conditioning films after adsorption of K36 (left panel) and K72 (right panel). Recombinant cationic SUPs interact with the negatively charged glycosylated mucins, causing collapse of the glycosylated structure through electrostatic interaction. In case of K72, not all positive charges engaged with the mucins and remain available for further interaction (right panel). c) Salivary conditioning films with adsorbed cationic SUPs and after renewed exposure to saliva. No mucins are recruited in the presence of adsorbed K36 (left panel), but remaining positive charges in the film possessing adsorbed K72 recruit mainly glycosylated mucins to form a soft mucinous layer over a compact SCF (right panel).

DETAILED DESCRIPTION OF THE INVENTION

Example 1

Design, Development and Characterization of Cationic Biolubricant SUPs

Materials

All chemicals were used as received without any further purification. The pUC19 cloning vector, restriction enzymes, and GeneJET™ Plasmid Miniprep kit were purchased from Fermentas (St. Leon-Rot, Germany). Digested DNA fragments were purified using QIAquick® spin miniprep kits from QIAGEN, Inc. (Valencia, Calif.). E. coli XL1-Blue competent cells for plasmid amplification were purchased from Stratagene (La Jolla, Calif.). Oligonucleotides for sequencing were ordered from Sigma-Aldrich (St. Louis, Mo.). A-cyano-4-hydroxycinnamic acid and internal standards trypsinogen and enolase for mass spectrometry were purchased from LaserBio Labs (Sophia-Antipolis, France). Ultrapure water, resistivity >18.2 MΩ·cm was used for all experiments.

Gene Oligomerization:

Integrity of DNA sequence was verified by sequencing of coding and complementary DNA strand after each cloning step (SequenceXS, Leiden, The Netherlands). SUP monomer gene SUP K9, encoding for the polypeptide [GVGVP(SEQ ID NO: 2(GKGVP)(SEQ ID NO: 1)$_9$], was ordered from Entelechon (Regensburg, Germany) and was delivered in the pEN vector. As the recognition sites of restriction enzymes PflMI and BglI had to be preserved, one valine residue per ten pentapeptide repeats was incorporated instead of a lysine residue during each oligomerization step. All cloning steps were performed according to standard molecular biology methods. SUP K9 was transferred into the standard cloning vector pUC19, digested with EcoRI and HinDIII. Gene oligomerization was performed as described by Meyer and Chilkoti.[26] Genes of correct length were identified by gel electrophoresis following plasmid digestion with EcoRI and HinDIII and sequencing (ServiceXS, Leiden, The Netherlands).

Protein Expression and Purification:

Genes coding for K36 and K72 were cloned into the expression vector pET25b(+)-SfiIHis6 as described before.[18] Escherichia coli BLR (DE3) (Novagen Inc., San Diego, Calif.) were transformed with pET25b(+)-SfiIHis6 containing the respective SUP genes. For protein production, Terrific Broth medium (TB; 12 g/L tryptone, 24 g/L yeast extract) enriched with phosphate buffer (2.31 g/L $KH_2PO_4$, 12.54 g/L $K_2HPO_4$) and glycerol (4 mL/L), and supplemented with 100 µg/mL ampicillin was inoculated with an overnight starter culture to an initial optical density at 600 nm ($OD_{600}$) of 0.1 and incubated at 37° C. with orbital agitation at 250 rpm until $OD_{600}$ reached 0.7. Cultures were shifted to 30° C., for additional 16 h. Cells were harvested by centrifugation (7,000 g, 20 min, 4° C.), resuspended in lysis buffer (10 mM TrisHCl, pH 8.0, 300 mM NaCl, 20 mM imidazole) to an $OD_{600}$ of 100 and disrupted with a constant cell disrupter (Constant Systems Ltd., Northands, UK). Cell debris was removed by centrifugation (40,000 g, 90 min, 4° C.). Polypeptides were purified from the supernatant under native conditions by Ni-sepharose chromatography (GE Healthcare). Protein-containing fractions were dialyzed extensively against ultrapure water. Purified polypeptides were frozen in liquid nitrogen, lyophilized and stored at −17° C. until further use.

Protein Characterization:

Concentrations of purified SUPs were determined by measuring absorbance at 280 nm on a SpectraMax M2 (Molecular Devices, Sunnyvale, Calif.). Protein purity was determined by sodium dodecyl sulfate polyacrylamide gel electrophoresis (SDS-PAGE) on a 12% polyacrylamide gel according to Laemmli.[27] Gels were stained with coomassie staining solution (40% methanol, 10% glacial acetic acid, 1 g/L Brilliant Blue R250). Photographs of the gels were taken with a LAS-3000 Image Reader (Fuji Photo Film GmbH, Dusseldorf, Germany). Both K36 and K72 showed reduced electrophoretic mobility compared to a commercial molecular weight standard, a well-known phenomenon for elastin-like polypeptides.[26,28] Mass spectrometric analysis was performed using a 4800 MALDI-TOF/TOF Analyzer (Applied Biosystems, Foster City, Calif., USA) in the linear positive mode. The protein samples were mixed 1:1 v/v with a recrystallized a-cyano-4-hydroxycinnamic acid matrix (10 mg/mL in 50% acetonitrile and 0.1% trifluoro acetic acid, LaserBio Labs). Mass spectra were analyzed and calibrated internally with the Data Explorer software, version 4.9 (Applied Biosystems, Foster City, Calif., USA). Trypsinogen (MW=23, 980) and enolase (MW=46,672) were used as calibration standards for K36 (expected MW=18,888) and K72 (expected MW=36,313), respectively.

Saliva Collection:

Saliva from twenty healthy volunteers (10 men, 10 women, average age 30±8 years) was collected into ice-chilled cups after stimulation of flow by chewing Parafilm®. Volunteers gave their informed consent to saliva donation, in agreement with the guidelines set out by the Medical-Ethical-Committee at the University-Medical-Center-Groningen, The Netherlands. After saliva was pooled and centrifuged at 12,000 g, 15 min, 4° C., phenylmethylsulfonylfluoride was added to a concentration of 1 mM as a protease-inhibitor. The solution was again centrifuged, dialyzed for 24 h, 4° C. against demineralized water, and freeze-dried for storage. Lyophilized stock was prepared by mixing freeze-dried material originating from 2 L of saliva. Reconstituted saliva was prepared from the lyophilized stock by dissolution of 1.5 mg/mL in buffer (2 mM potassium phosphate, 1 mM $CaCl_2$, 50 mM KCl, pH 6.8).

Quartz Crystal Microbalance with Dissipation Monitoring:

Structural softness and formation kinetics of SCFs were studied using a QCM-D device, model Q-sense E4 (Q-sense, Gothenburg, Sweden). Au-coated quartz crystals with 5 MHz were used as substrata. Before each experiment, crystals were cleaned by 10 min UV/ozone treatment, followed by immersion into a 3:1:1 mixture of ultrapure-water, $NH_3$ and $H_2O_2$ at 70° C. for 10 min, drying with $N_2$ and another UV/ozone treatment. QCM-D chamber is disc-shaped with the inlet and outlet facing the crystal surface. The chamber was perfused with buffer by peristaltic pump (Ismatec SA, Glattbrugg, Switzerland), when stable base lines for both frequency and dissipation at third harmonics were achieved, saliva was introduced. Saliva was perfused through the chamber at 25° C. for 2 h, flow rate of 50 μL/min, corresponding with a shear rate of 3 $s^{-1}$ after which, the chamber was perfused with buffer or 0.05% w/v of SUP for 2 min and followed by another 2 h of salivary flow to form a secondary SCF denoted as S-SCF. In between steps, the chamber was perfused with buffer for 15 min or till a stable frequency shift of less than 2 Hz over 10 min was observed. The shear rate in the QCM-D represents a low oral salivary flow.[29] Frequency and dissipation were measured real-time during perfusion. After experiments, crystals were removed from the QCM-D and immediately used for further experiments.

Colloidal Probe Atomic Force Microscopy:

Friction force, surface topography and repulsive force range toward a colloidal AFM probe[30] were measured in buffer with an AFM (Nanoscope IV Dimension™3100) equipped with a Dimension Hybrid XYZ SPM scanner head (Veeco, N.Y., USA) on the differently adsorbed SCFs. Rectangular, tipless cantilevers were calibrated for their torsional and normal stiffness using AFM Tune IT v2.5 software.[31] The normal stiffness ($K_n$) was between 0.01-0.04 N/m and the torsional stiffness ($K_t$) between 2-4 $10^{-9}$ Nm/rad. Subsequently, a silica-particle of 4.74 μm diameter (d) (Bangs laboratories, Fishers, Ind., USA) was glued to a cantilever with an epoxy glue (Pattex, Brussels, Belgium). The deflection sensitivity (a) of the colloidal probe was recorded at a constant compliance with bare crystal in buffer to calculate the normal force ($F_n$) applied using $$F_n = \Delta V_n * a * K_n \quad (2)$$

where $\Delta V_n$ is the voltage output from the AFM photodiode due to normal deflection of the colloidal probe. The torsional stiffness and geometrical parameters of the probe were used to calculate the friction force ($F_f$)[19, 32] according to $$F_f = \frac{\Delta V_L * K_t}{2 * \delta * \left(d + \frac{t}{2}\right)} \quad (3)$$

where t is the thickness of the cantilever, δ is the torsional detector sensitivity of the AFM and $\Delta V_L$ corresponds to the voltage output from the AFM photodiode due to lateral deflection of the probe. Lateral deflection was observed at a scanning angle of 90 degrees over a scan area of 5×5 μm² and a scanning frequency of 1 Hz. The colloidal probe was incrementally loaded and unloaded up to a normal force of 35 nN. At each normal force, 10 friction loops were recorded to yield the average friction force. Repulsive force-distance curves between a colloidal probe and the films were obtained at a trigger threshold of 10 nN and an approach and retraction velocity of 10 μm/s. The repulsive force range (D) was determined at a point where colloidal tip starts experiencing the repulsive force >1 nN between the two interacting surfaces.

X-Ray Photoelectron Spectroscopy:

Glycosylation of the adsorbed SCFs was determined by using XPS (S-probe, Surface Science Instruments, Mountain View, Calif., USA). Films adsorbed on Au-coated quartz crystals as removed from the QCM-D, were dried in the pre-vacuum chamber of the XPS, and then subjected to a vacuum of $10^{-7}$ Pa. X-rays (10 kV, 22 mA, spot size 250×1000 μm), were produced using an aluminum anode. Scans in the binding energy range of 1-1100 eV were made at low resolution (pass energy 150 eV). The area under each peak was used to yield elemental surface concentrations for C, O, N, and Au after correction with sensitivity factors provided by the manufacturer. The $O_{1S}$ peak was split into three components for oxygen involved in amide groups (C=O—N; 531.3 eV), carboxyl groups (C—O—H; 532.7 eV) and oxygen arising from the crystal. Accordingly, the fraction of the $O_{1s}$ peak at 532.7 eV (% $O_{532.7}$) was used to calculate the amount of oxygen involved in glycosylated moieties (% $O_{glyco}$) and amides (% $O_{amides}$).

$$\% O_{glyco} = \% O_{532.7} * \% O_{total} \quad (4)$$

$$\% O_{amide} = \% O_{531.3} * \% O_{total} \quad (5)$$

where % $O_{total}$ is the total percentage of oxygen.

Results

Two exemplary SUPs with the amino acid sequences GAGP(SEQ ID NO: 8)[(GVGVP)(SEQ ID NO: 2)(GKGVP)(SEQ ID NO: 1)$_9]_4$GWPH$_6$(SEQ ID NO: 10) (K36) and GAGP(SEQ ID NO: 8)[(GVGVP)(SEQ ID NO: 2)(GKGVP)(SEQ ID NO: 1)$_9]_8$GWPH$_6$(SEQ ID NO: 10) (K72) were fabricated by recombinant protein expression in *Escherichia coli*. The gene sequence and respective a amino acid sequence of the monomer are shown below.

```
                                                   (SEQ ID NO: 12)
EcoRI                   PflMI
A ATT CAT ATG GGC CAC GGC GTG GGT GTT CCG GGC AAA
                  G    V   G    V   P    G   K

GGT GTT CCG GGT AAA GGT GTG CCG GGC AAA GGT GTT
 G   V   P   G   K   G   V   P   G   K   G   V

CCT GGT AAA GGT GTG CCG GGT AAA GGT GTG CCG GGT
 P   G   K   G   V   P   G   K   G   V   P   G

AAA GGT GTA CCA GGT AAA GGT GTT CCG GGT AAA GGC
 K   G   V   P   G   K   G   V   P   G   K   G

BglI         HindIII
GTT CCG GTT AAA GGT GTG CCG GGC GGG CTG GAA TA
 V   P   G   K   G   V   P
```

The gene length was verified using gel electrophoresis (data not shown). Typical yields were 45 mg (K36) and 40 mg (K72) of purified protein per liter of culture. Purified polypeptides were separated on a SDS-PAGE gel. Mass spectra yielded sharp peaks for both variants i.e. K36 and K72) and their masses were 18,932±20 Da for K36 and 36,330±30 Da for K72. The formation of SCFs on gold (Au) coated quartz crystals and the effects of their exposure to recombinant K36 and K72 or buffer, followed by renewed adsorption of salivary proteins, were observed real-time in the QCM-D, as presented in FIG. 1a-c.

Figure 1D:
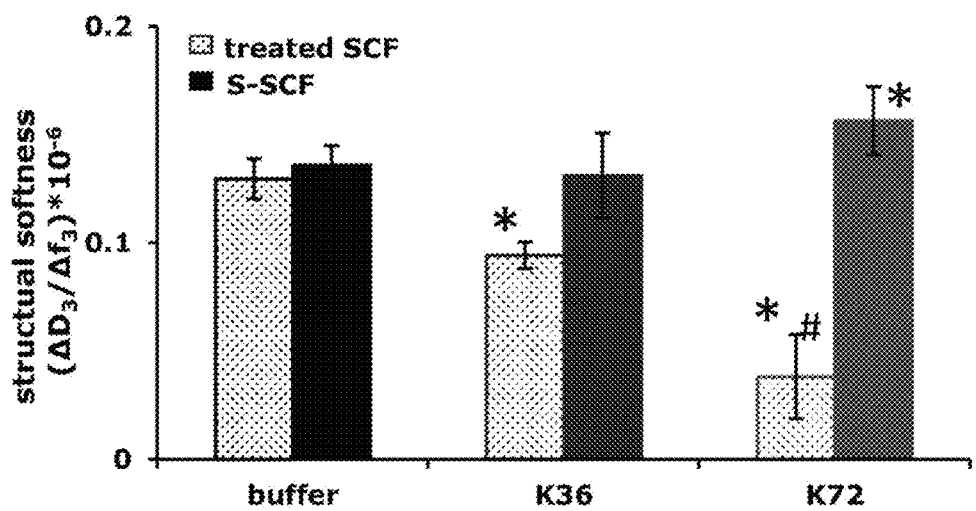

Exposure of an existing SCF to buffer (FIG. 1a) yielded a small change in the oscillating sensor frequency ($\Delta f_3$) and dissipation ($\Delta D_3$), whereas exposure to K36 (FIG. 1b) and K72 (FIG. 1c) solutions caused significant decreases in $\Delta f_3$ and $\Delta D_3$ that were largest for K72. Subsequent removal of the protein solution by perfusing the QCM-D chamber with buffer indicated a structural decrease in the softness of the SCFs, expressed as the ratio ($\Delta D_3/\Delta f_3$). Again, this effect was larger after exposure to K72 solution than after exposure to K36 solution (FIG. 1d). Renewed salivary exposure over the SCFs was initiated immediately after treatment with buffer or recombinant protein solutions to form S-SCFs (FIG. 1a-c) because such experimental conditions reflect best the in vivo situation of immediate reflow of saliva in the oral cavity. Renewed perfusion of the QCM-D chamber with saliva did not affect the structural softness of the S-SCF with only buffer without recombinant SUPs (FIG. 1d), but S-SCF with K36 solution became softer again to a level comparable to S-SCF without recombinant SUPs. The S-SCFs with K72, however, were significantly ($p<0.05$, two tailed Student t-test) softer than S-SCFs with K36.

Figure 2A:
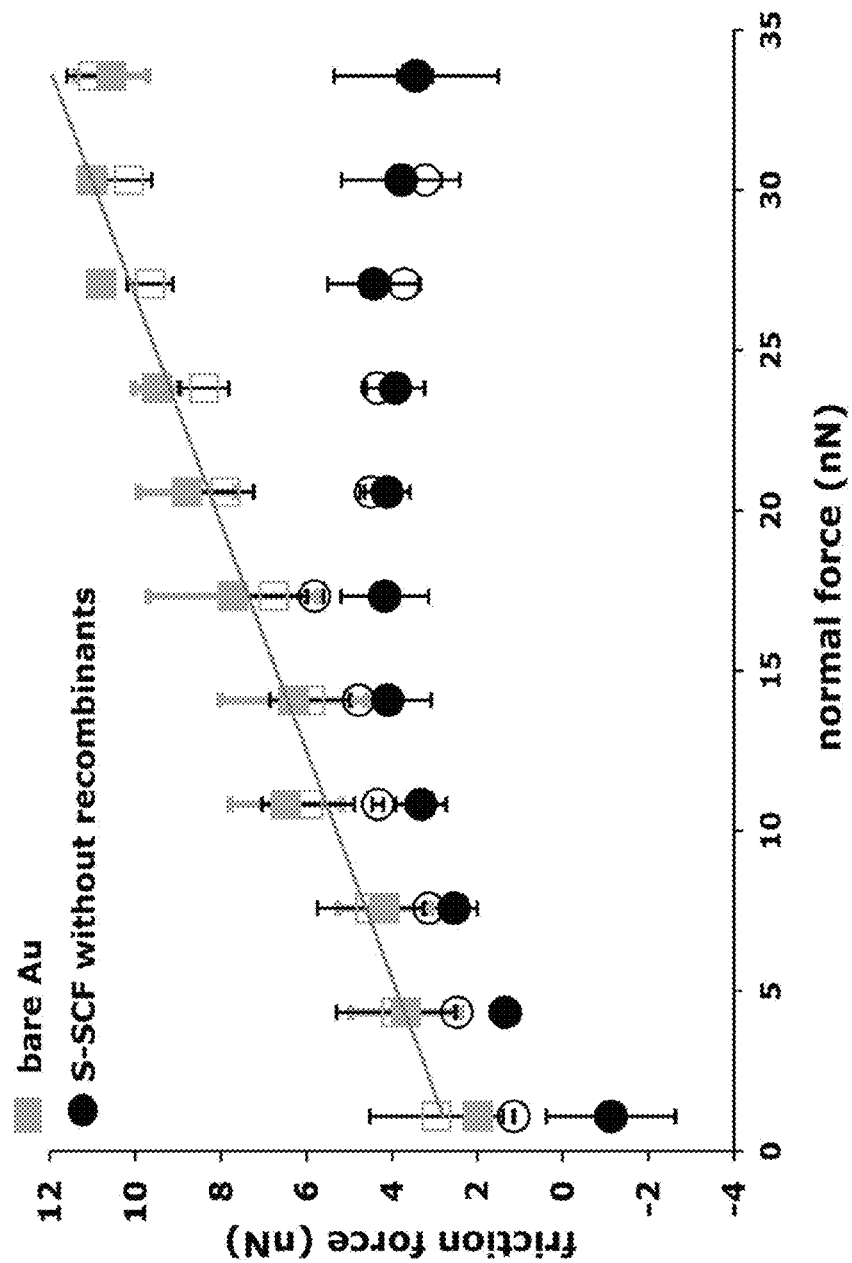
Figure 2B:
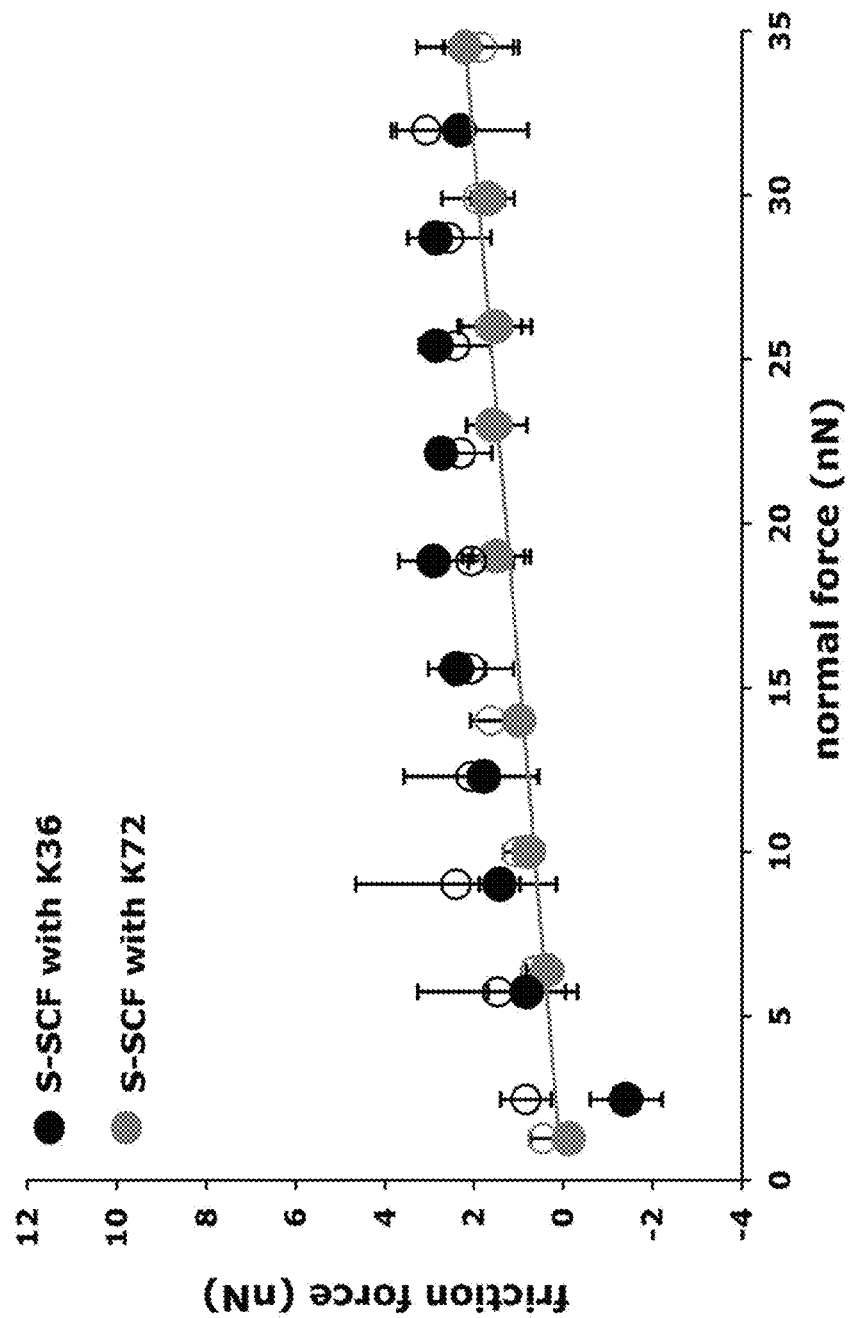
Figure 2C:
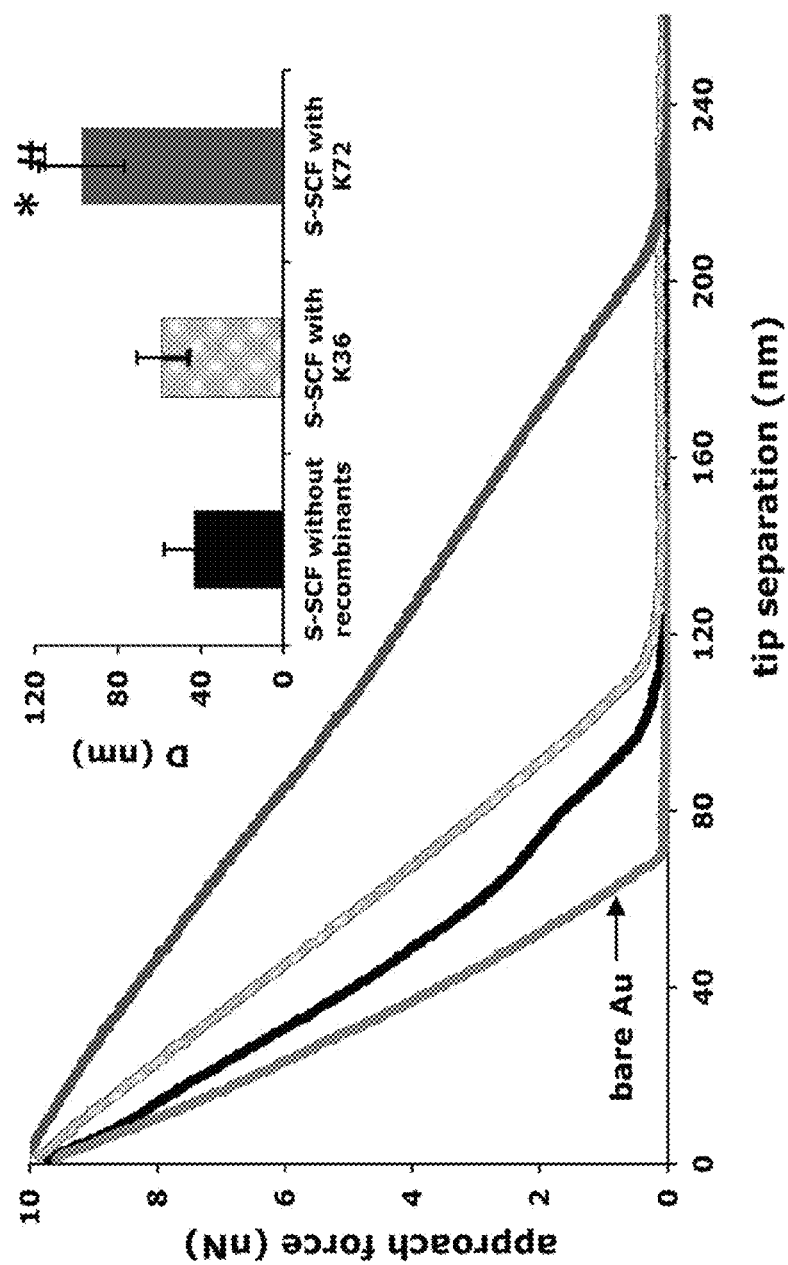
Figure 2D:
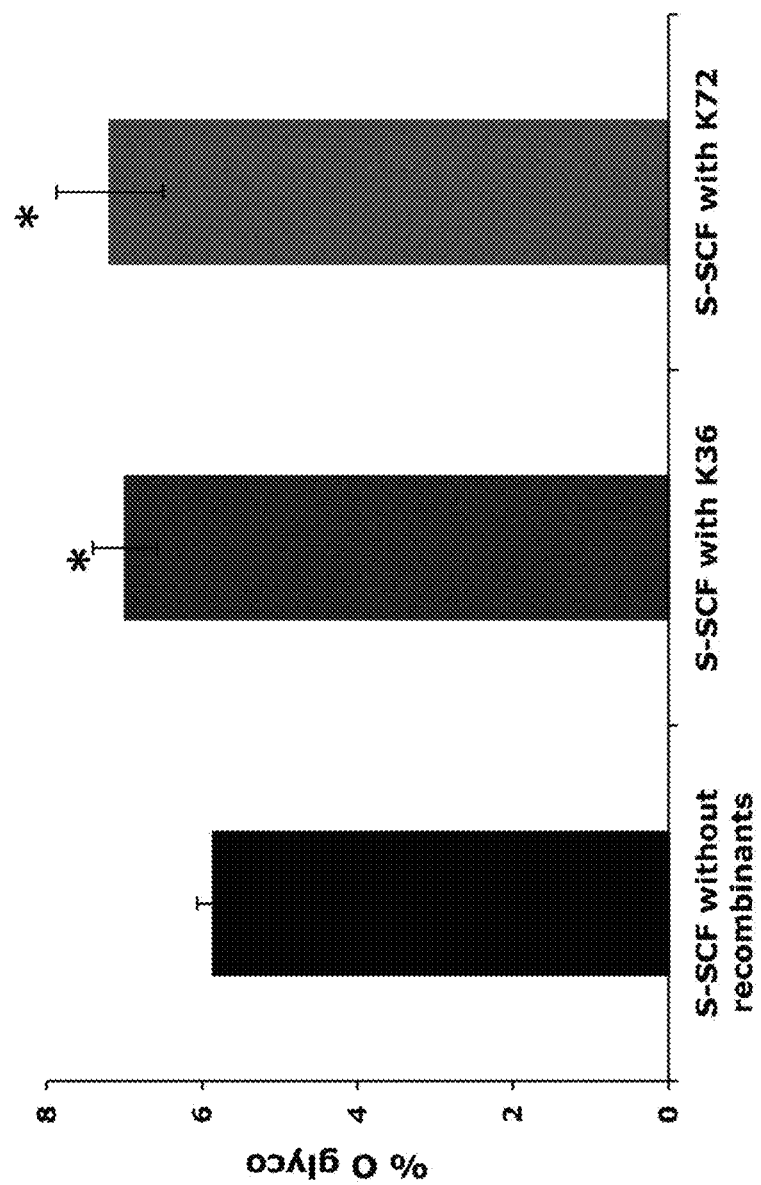

In a next step, the lubrication properties of the SUP-modified films were investigated by colloidal probe AFM. Friction forces on bare Au-coated crystals increased linearly ($R^2=0.95$) with normal force up to 35 nN, corresponding to a coefficient of friction (COF) of 0.28 (FIG. 2a). Upon adsorption of a SCF, friction forces appeared almost two times lower than on Au-coated crystals with a COF of 0.19, and linearity broke down at normal forces above 14 nN. Note that the negative friction forces at a normal force of 1.5 nN represent the known limitation of AFM to measure very low friction forces.[19] However, measurements on S-SCFs with recombinant SUPs clearly showed lower friction forces (FIG. 2b). Linearity corresponding to a COF of 0.08 persisted up to a normal force of 20 nN for K36, while linearity ($R^2=0.94$) corresponding to an extremely low COF of 0.06 existed over the entire range of normal forces applied for K72-modified films, indicative of a high structural integrity. Contact of the AFM colloidal probe with the Au-coated quartz crystal (FIG. 2c) shows a hard material compared with the softer S-SCFs due to long-range repulsive forces between S-SCFs and the approaching colloidal probe. The repulsive force range arising from the S-SCFs increased with the number of positive charges after adsorption of recombinant cationic SUPs (FIG. 2c). To gain more insight into the structural composition of the S-SCFs, XPS was applied to measure the degree of glycosylation, which is related to the water content of the surface (FIG. 2d). Glycosylation in the S-SCFs with no adsorbed SUPs amounts to 5.8±0.8% and increases with the molecular weight of the adsorbed SUPs to 6.9±0.3% and 7.2±0.6% in SCFs with K36 and K72, respectively.

From the measurements described above one can conclude that cationic recombinant SUPs adsorb on SCFs and decrease their structural softness, i.e. increase their rigidity. SUPs carrying more positive charges create more rigid films, and more efficiently recruit salivary proteins to form a SCF with a thicker globular structure and higher degree of glycosylation, generating a longer repulsive force range and more stable, low friction. Patients with oral dryness symptoms have reduced salivary flow rates, but naturally occurring salivary proteins are always present. This study is the first in which naturally occurring salivary proteins are recruited through the adsorption of recombinant, cationic SUPs to improve several parameters crucial for effective biolubrication. Our approach represents a groundbreaking strategy for artificial biolubrication, where additives act in concert with and enhance the natural lubricants rather than simply replacing them. A proof of principle was obtained for oral lubrication the most challenging environment for biolubrication, but similar recruitment mechanisms can be applied in other parts of the human body (e.f. ocular or vaginal cavity) as well.

Figure 3A:
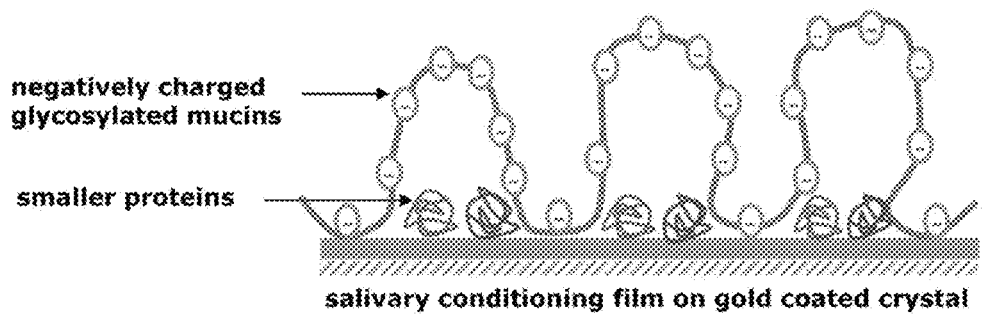
Figure 3B:
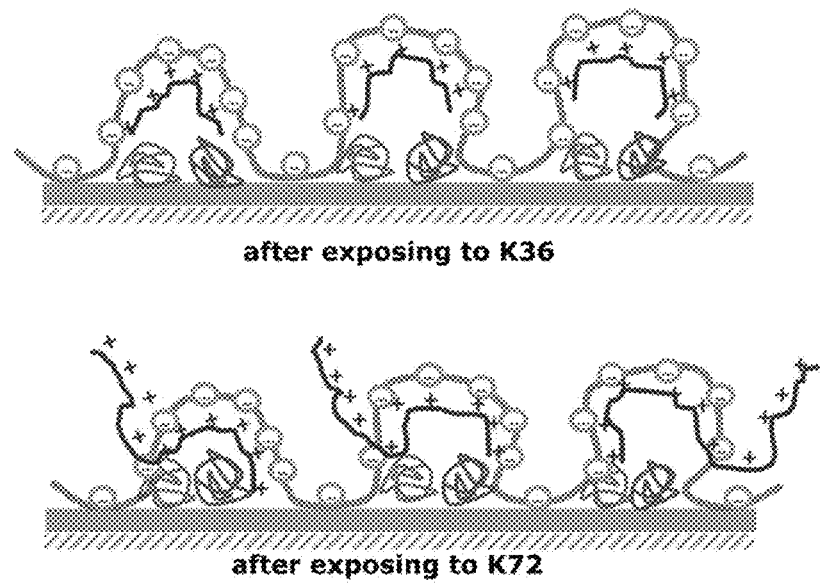
Figure 3C:
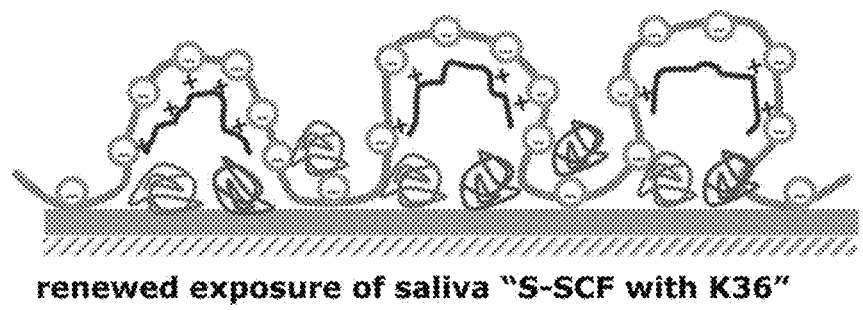
Figure 3C:
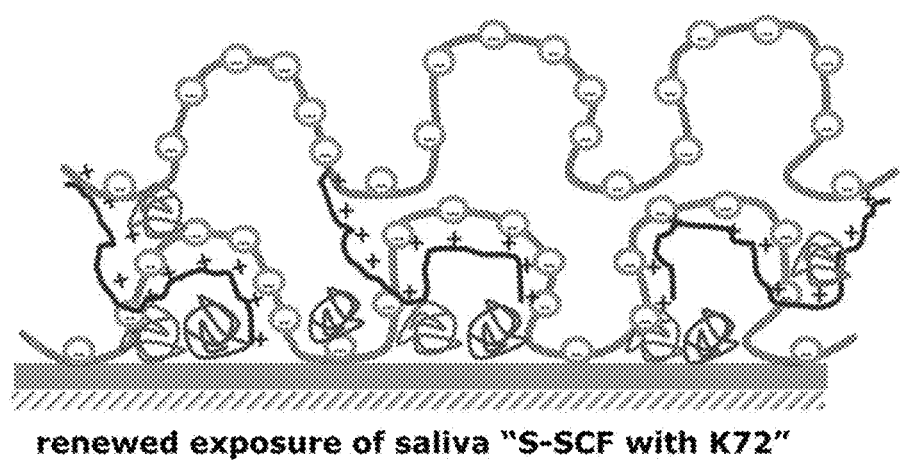

SCF is composed of glycosylated, high-molecular weight mucins (0.25 to 20 MDa) that adsorb in loops and trains (with a molecular aspect ratio of up to 1/1000)[20] and thereby provide a scaffold to hold and retain water molecules at the surface, while adsorbed smaller proteins like proline-rich proteins, histatins, lysozymes, and amylases may be found underneath the loops and between the trains (FIG. 3a).[21] Based on the measurements presented above, we suggest a model for the interaction of cationic SUPs with an existing SCF and for how the adsorbed cationic proteins may be further involved in the recruitment of salivary proteins during renewed exposure to saliva. K36 and K72 bind to the negatively charged mucins leading to elimination of electrostatic stabilization of the adsorbed film and its subsequent collapse, forming a rigid structure (FIG. 3b). K72 is a polypeptide consisting of more than 400 amino acids with 72 positively charged groups evenly distributed along the polymer backbone. The higher number of positive charges in K72 compared with K36 neutralizes negative charges in the SCF, but importantly not all positive charges of K72 are engaged in interaction with negative charges in the SCF and positive charges of adsorbed K72 remain available for further interaction with negative charges. This can be concluded from zeta potential measurements (data not shown), showing more positive charge on SCFs exposed to K72 than on K36-treated and untreated SCFs (data not shown). Thus uncompensated positive surface charges of adsorbed K72 on a SCF can trigger further recruitment of negatively charged glycosylated mucins during renewed exposure to saliva (FIG. 3b; right panel), resulting in a softer highly hydrated over-layer (FIG. 3c). This recruitment process rejuvenates the film, as it can bind to more water molecules. This is one critical step beyond simply restoring the film structure, as observed in SCFs formed after reflow of saliva over K36-treated and buffer-treated SCFs.

The rigid and hydrated S-SCF, modified with adsorbed K72 and after renewed exposure to saliva, shows low friction forces and a structural integrity that is not compromised at higher contact pressures, in contrast to films containing K36 or untreated films. The breakdown of structural integrity in these latter films can be seen from the discontinuity in the linearity of friction force against the normal force.[23,24] In order to determine the mechanical strength of the S-SCFs, we have applied Von Mises distortion energy criterion that relates the normal force at which the discontinuity arises ($f_L$) to the yield strength ($\sigma_y$) of the films[24,25] through $$\sigma_y = \frac{1}{\sqrt{2}}\left[2\left(\frac{3*f_L}{2*\pi*R_{tip}*\delta}\right)^2 + 6\left(\frac{3*f_L}{2*\pi*R_{tip}*\delta}\right)\right]^{0.5} \quad (1)$$

where $R_{tip}$ is the radius of the colloidal probe (2.37 μm), δ is the elastic displacement of the film determined from a Hertzian fit to the force-distance curves as obtained by colloidal probe AFM and $f_f$ is the friction force at $f_L$. Accordingly, yield strength for S-SCF in absence of recombinant cationic SUPs is 80±12 kPa, increasing to 102±8 kPa in the presence of adsorbed K36. In contrast, no discontinuity in the linearity of friction force against the normal force was observed for K72-treated films within the range of normal forces applied, indicating that the yield strength of S-SCFs in presence of K72 exceeds 102 kPa. This increase in the yield strength can be attributed to improved cohesive strength in the adsorbed films, against the applied shear force.

In conclusion, an ideal biolubricant-like artificial saliva should lubricate the oral surfaces and at the same time sustain this lubrication for lasting benefits. Here we demonstrate that non-toxic, recombinant cationic SUPs adsorb on SCFs to recruit further glycosylated mucins from saliva, provided the number of positive charges is sufficiently high. These hydrated and rigid films improve interfacial lubrication and maintain their structural integrity upon high contact pressures. Current generations of artificial salivas are inadequate to restore oral lubrication on a lasting basis. Cationic recombinant SUPs as additives, however, go even beyond restoration to rejuvenation of the film, affording effective lubrication under conditions of reduced availability of naturally occurring proteins. On the basis of the cooperative layer-by-layer mechanism laid out here, cationic protein polyelectrolytes show great promise for restoring impaired biolubrication.

Example 2

Oral Composition Comprising SUP

A translucent oral composition e.g. for use as artificial saliva composition comprising biolubricant peptide (0.05% w/v) and optionally bovine submandibular Mucins (3.5% w/v), and has a pH value of between 5 and 6.

Example 3

Ocular Composition Comprising SUP

A typical ocular composition includes the ingredients listed below,
0.1% w/w to about 2% w/w demulcent.:
Biolubricant peptide 0.05% w/v
Sodium Chloride: 0.4% w/v
Potassium Chloride 0.038
Polyquaternium-1 0.00001-0.001
NaOH/HCl q.s. pH 7.4
Purified Water q.s. to 100.

Example 4

Use of SUP for Treating Dry Mouth

The composition of example 2 is used to treat a patient with dry mouth. The patient applied the composition of example 2 to an oral cavity, swished thoroughly for about 30 seconds to about one minute, then spit out the composition, and repeated this application 2-3 times per day. The patient noticed relief from (mitigation of) dry mouth and irritation. The patient noticed a moist and a clean and refreshed feeling within the mouth. The patient also noticed that there was no burning sensation noticed with application of the composition.

REFERENCES

1) J. Klein, *Polym. Adv. Technol.*, 2012, 23, 729-735
2) J. M. Meijer, P. M. Meiners, J. J. R. Huddleston Slater, F. K. L. Spijkervet, C. G. M. Kallenberg, A. Vissink, H. Bootsma, *Rheumatology* 2009, 48,1077.
3) E. K. Akpek, K. B. Lindsley, R. S. Adyanthaya, R. Swamy, A. N. Baer, P. J. McDonnell, *Ophthalmology* 2011, 118, 1242.
4) C. M. Stewart, K. M. Berg, S. Cha, W. M. Reeves, *J. Am. Dent. Assoc.* 2008, 139, 291.
5) N. Schoofs, *J. Obstet. Gynecol. Neonatal. Nurs.* 2003, 32, 589.
6) C. T. Peace, W. Shattles, N. K. Barrett, R. N. Maini, *Rheumatology*, 1993, 32, 609.
7) S. Lee, N. D. Spencer, *Science*, 2008, 319, 575.
8) B. Zappone, M. Ruths, G. W. Greene, G. D. Jay, J. N. Israelachvili, *Biophys. J.* 2007, 92, 1693.
9) I. C. H. Berg, M. W. Rutland, T. Arnebrant, *Biofouling* 2003, 19, 365.
10) M. Hannig, M. Balz *Caries Res.* 1999, 33, 372.
11) A. Joiner, A. Schwarz, C. J. Philpotts, T. F. Cox, K. Huber, M. Hannig, *J. Dent.* 2008, 36, 360.
12) B. Dejak, A. Mlotkowski, M. Romanowicz, *J. Prosthet. Dent.* 2003, 90, 591.
13) K. C. Morrell, W. A. Hodge, D. E. Krebs, R. W. Mann, *Proc. Natl. Acad. Sci. USA* 2005, 102, 14819.
14) A. Mariotti in *xPharm: The Comprehensive Pharmacology Reference*, eds S. J. Enna, David B. Bylund (Elsevier, New York) 2004, 1.
15) S. Hahnel, M. Behr, G. Handel, R. Bargers, *Suppor. Care Cancer* 2009, 17, 1331.
16) M. Salomaki, J. Kankare, *Biomacromolecules* 2009, 10, 294.
17) U. Raviv, S. Giasson, N. Kampf, J. F. Gohy, R. Jérome, J. Klein, *Nature* 2003, 425, 163.
18) A. Kolbe, L. L. del Mercato, A. Z. Abbasi, P. R. Gil, S. J. Gorzini, W. H. Huibers, B. Poolman, W. J. Parak, A. Herrmann, *Macromol. Rapid Commun.* 2011, 32, 186.
19) T. Pettersson, A. Naderi, R. Makuska P. Claesson, *Langmuir* 2008, 24, 3336.
20) J. K. Sheehan, K. Oates, T. Carlsted, *Biochem. J* 1986, 239, 147-153
21) D. H. Veeregowda, H. J. Busscher, A. Vissink, D. J. Jager, P. K. Sharma, H. C. van der Mei, *PLOS One* 2012, 7, e42600.
22) O. Svensson, L. Lindh, M. Cardenas, L. Arnebrant, *J. Colloid Interf. Sci.* 2006, 299, 608.
23) J. Yu, X. Banquy, G. W. Greene, D. D. Lowrey, J. N. Israelachvili, *Langmuir* 2011, 28, 2244.

24) J. Sotres, A. Barrantes, T. Arnebrant, *Langmuir* 2011, 27, 9439.
25) L. Y. Wang, Z. F. Yin, J. Zhang, C. Chen, S. Hsu, *Wear* 2000, 237, 155.
26) D. E. Meyer, A. Chilkoti, *Biomacromolecules* 2002, 3, 846.
27) U. K. Laemmli, *Nature* 1970, 227, 680.
28) D. T. McPherson, T. David, J. Xu, D. W. Urry, *Protein Expr. Purif.* 1996, 7, 51.
29) S. Watanabe, C. Dawes, *J. Dent. Res.* 1990, 69, 1150.
30) W. Ducker, T. Senden, M. Pashley, *Nature* 1991, 353, 239.
31) T. Pettersson, N. Nordgren, M. W. Rutland, A. Feiler, *Rev. Sci. Instrum.* 2007, 78, 093702.
32) T. Pettersson, A. Dedinaite, *J. Colloid. Interf. Sci.* 2008, 324, 246.

INCORPORATION OF SEQUENCE LISTING

Incorporated herein by reference in its entirety is the Sequence Listing for the application. The Sequence Listing is disclosed on a computer-readable ASCII text file titled, "subs_seq_list_294_432.txt", created on Apr. 22, 2014. The file is 9.64 kb in size.

The invention claimed is:

1. A proteinaceous biolubricant substance comprising the general formula Head-(SEQ ID NO: 1)(SEQ ID NO: 2)$_9$]$_n$-Tail, wherein
   n is ≥5;
   Head is an amino acid sequence of 3 to 12 amino acids; and
   Tail is an amino acid sequence of at least 3 amino acids.

2. The proteinaceous biolubricant substance according to claim 1, wherein n is ≥6.

3. The proteinaceous biolubricant substance according to claim 1, wherein Head is SEQ ID NO: 8.

4. The proteinaceous biolubricant substance according to claim 1, further comprising a protein tag sequence allowing for affinity purification of the substance.

5. The proteinaceous biolubricant substance according to claim 4, wherein head or Tail comprises a His-tag.

6. The proteinaceous biolubricant substance according to claim 1, having a linear structure.

7. A branched proteinaceous biolubricant substance having a degree n of branching, wherein each of the branches comprises the amino acid sequence (SEQ ID NO: 1)m, and wherein n times m is at least 40.

8. The branched biolubricant substance according to claim 7, wherein m is in the range of 2-10.

9. The branched biolubricant substance according to claim 7, wherein n is at least 5.

10. An isolated nucleic acid sequence encoding a biolubricant substance according to claim 1.

11. An expression vector comprising an isolated nucleic acid according to claim 10.

12. A non-human host cell comprising an expression vector according to claim 11.

13. A composition comprising a biolubricant substance according to claim 1, and a pharmaceutically acceptable carrier, diluent or excipient.

14. A composition comprising a biolubricant substance according to claim 7 and a pharmaceutically acceptable carrier, diluent or excipient.

15. An oral care composition that alleviates dry mouth comprising a proteinaceous biolubricant substance comprising [(SEQ ID NO: 1)$_9$]n, wherein n is ≥5.

16. An oral care composition that alleviates dry mouth comprising a proteinaceous biolubricant substance having a degree of n of branching, each of the branches comprising (SEQ ID NO: 1)m wherein n times m is at least 40.

17. A method for treating or preventing a condition associated with impaired lubrication of a bodily cavity, comprising administering to a subject in need thereof a therapeutically effective amount of a biolubricant substance according to claim 1.

18. The method according to claim 17, wherein said bodily cavity is the oral, ocular or vaginal cavity.

19. The method according to claim 17, wherein said subject is a mammal.

20. The method according to claim 17, wherein said condition is xerostomia, xerophthalmia, Atrophic Vaginitis (vaginal dryness) or Sjogren's syndrome.

21. A method for treating or preventing a condition associated with impaired lubrication of a bodily cavity, comprising administering to a subject in need thereof a therapeutically effective amount of a biolubricant substance according to claim 7.

22. The method according to claim 21, wherein said bodily cavity is the oral, ocular or vaginal cavity.

23. The method according to claim 21, wherein said subject is a mammal.

24. The method according to claim 21, wherein said condition is xerostomia, xerophthalmia, Atrophic Vaginitis (vaginal dryness) or Sjogren's syndrome.

25. A method for treating or preventing a condition associated with impaired lubrication of a bodily cavity, comprising administering to a subject in need thereof a therapeutically effective amount of a composition comprising a biolubricant substance according to claim 13.

26. The method according to claim 25, wherein said bodily cavity is the oral, ocular or vaginal cavity.

27. The method according to claim 25, wherein said subject is a mammal.

28. The method according to claim 25, wherein said condition is xerostomia, xerophthalmia, Atrophic Vaginitis (vaginal dryness) or Sjogren's syndrome.

29. A method for treating or preventing a condition associated with impaired lubrication of a bodily cavity, comprising administering to a subject in need thereof a therapeutically effective amount of a biolubricant substance according to claim 14.

30. The method according to claim 29, wherein said bodily cavity is the oral, ocular or vaginal cavity.

31. The method according to claim 29, wherein said subject is a mammal.

32. The method according to claim 29, wherein said condition is xerostomia, xerophthalmia, Atrophic Vaginitis (vaginal dryness) or Sjogren's syndrome.

* * * * *

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: building block biolubricant

<400> SEQUENCE: 1

Gly Lys Gly Val Pro
1               5

<210> SEQ ID NO 2
<211> LENGTH: 5
<212> TYPE: PRT
<213> ORGANISM: Artificial Sequence
<220> FEATURE:
<223> OTHER INFORMATION: building block of biolubricant

<400> SEQUENCE: 2

Gly Val Gly Val Pro
1               5

<210> SEQ ID NO 3
<211> LENGTH: 45
<212> TYPE: PRT
<213> ORGANISM: Artificial Sequence
<220> FEATURE:
<223> OTHER INFORMATION: biolubricant

<400> SEQUENCE: 3

Gly Lys Gly Val Pro Gly Lys Gly Val Pro Gly Lys Gly Val Pro Gly
1               5                  10                  15

Lys Gly Val Pro Gly Lys Gly Val Pro Gly Lys Gly Val Pro Gly Lys
            20                  25                  30

Gly Val Pro Gly Lys Gly Val Pro Gly Lys Gly Val Pro
        35                  40                  45

<210> SEQ ID NO 4
<211> LENGTH: 5
<212> TYPE: PRT
<213> ORGANISM: Artificial Sequence
<220> FEATURE:
<223> OTHER INFORMATION: building block elastin-like protein

<400> SEQUENCE: 4

Val Pro Gly Val Gly
1               5

<210> SEQ ID NO 5
<211> LENGTH: 20
```

```
<212> TYPE: PRT
<213> ORGANISM: Artificial Sequence
<220> FEATURE:
<223> OTHER INFORMATION: motif elastin-like protein

<400> SEQUENCE: 5

Val Pro Gly Val Gly Val Pro Gly Val Gly Val Pro Gly Val Gly Val
1               5                   10                  15

Pro Gly Val Gly
            20

<210> SEQ ID NO 6
<211> LENGTH: 5
<212> TYPE: PRT
<213> ORGANISM: Artificial Sequence
<220> FEATURE:
<223> OTHER INFORMATION: cationic sequence

<400> SEQUENCE: 6

Gly Lys Gly Val Pro
1               5

<210> SEQ ID NO 7
<211> LENGTH: 6
<212> TYPE: PRT
<213> ORGANISM: Artificial Sequence
<220> FEATURE:
<223> OTHER INFORMATION: non-charged silk-like unit

<400> SEQUENCE: 7

Gly Ala Gly Ala Gly Ser
1               5

<210> SEQ ID NO 8
<211> LENGTH: 4
<212> TYPE: PRT
<213> ORGANISM: Artificial Sequence
<220> FEATURE:
<223> OTHER INFORMATION: head sequence biolubricant

<400> SEQUENCE: 8

Gly Ala Gly Pro
1

<210> SEQ ID NO 9
<211> LENGTH: 4
<212> TYPE: PRT
<213> ORGANISM: Artificial Sequence
<220> FEATURE:
<223> OTHER INFORMATION: tail sequence of biolubricant

<400> SEQUENCE: 9

Gly Gly Trp Pro
1

<210> SEQ ID NO 10
<211> LENGTH: 10
<212> TYPE: PRT
<213> ORGANISM: Artificial Sequence
<220> FEATURE:
<223> OTHER INFORMATION: tail sequence of biolubricant

<400> SEQUENCE: 10

Gly Gly Trp Pro His His His His His His
1               5                   10
```

<210> SEQ ID NO 11
<211> LENGTH: 10
<212> TYPE: PRT
<213> ORGANISM: Artificial Sequence
<220> FEATURE:
<223> OTHER INFORMATION: head sequence biolubricant

<400> SEQUENCE: 11

His His His His His His Gly Ala Gly Pro
1               5                   10

<210> SEQ ID NO 12
<211> LENGTH: 180
<212> TYPE: DNA
<213> ORGANISM: Artificial Sequence
<220> FEATURE:
<223> OTHER INFORMATION: DNA coding for monomer of biolubrucant
<220> FEATURE:
<221> NAME/KEY: CDS
<222> LOCATION: (17)..(166)

<400> SEQUENCE: 12
aattcatatg ggccac ggc gtg ggt gtt ccg ggc aaa ggt gtt ccg ggt aaa      52
                  Gly Val Gly Val Pro Gly Lys Gly Val Pro Gly Lys
                   1               5                  10 ggt gtg ccg ggc aaa ggt gtt cct ggt aaa ggt gtg ccg ggt aaa ggt      100
Gly Val Pro Gly Lys Gly Val Pro Gly Lys Gly Val Pro Gly Lys Gly
             15                  20                  25 gtg ccg ggt aaa ggt gta cca ggt aaa ggt gtt ccg ggt aaa ggc gtt      148
Val Pro Gly Lys Gly Val Pro Gly Lys Gly Val Pro Gly Lys Gly Val
         30                  35                  40 ccg gtt aaa ggt gtg ccg ggcgggctgg aata                              180
Pro Val Lys Gly Val Pro
45                  50

<210> SEQ ID NO 13
<211> LENGTH: 50
<212> TYPE: PRT
<213> ORGANISM: Artificial Sequence
<220> FEATURE:
<223> OTHER INFORMATION: Synthetic Construct

<400> SEQUENCE: 13

Gly Val Gly Val Pro Gly Lys Gly Val Pro Gly Lys Gly Val Pro Gly
1               5                   10                  15

Lys Gly Val Pro Gly Lys Gly Val Pro Gly Lys Gly Val Pro Gly Lys
                20                  25                  30

Gly Val Pro Gly Lys Gly Val Pro Gly Lys Gly Val Pro Val Lys Gly
            35                  40                  45

Val Pro
    50

<210> SEQ ID NO 14
<211> LENGTH: 213
<212> TYPE: PRT
<213> ORGANISM: Artificial Sequence
<220> FEATURE:
<223> OTHER INFORMATION: K36

<400> SEQUENCE: 14

Gly Ala Gly Pro Gly Val Gly Val Pro Gly Lys Gly Val Pro Gly Lys
1               5                   10                  15

Gly Val Pro Gly Lys Gly Val Pro Gly Lys Gly Val Pro Gly Lys Gly
                20                  25                  30

Val Pro Gly Lys Gly Val Pro Gly Lys Gly Val Pro Gly Lys Gly Val
        35                  40                  45

Pro Gly Lys Gly Val Pro Gly Val Gly Val Pro Gly Lys Gly Val Pro
    50                  55                  60

Gly Lys Gly Val Pro Gly Lys Gly Val Pro Gly Lys Gly Val Pro Gly
65                  70                  75                  80

Lys Gly Val Pro Gly Lys Gly Val Pro Gly Lys Gly Val Pro Gly Lys
                85                  90                  95

Gly Val Pro Gly Lys Gly Val Pro Gly Val Gly Val Pro Gly Lys Gly
            100                 105                 110

Val Pro Gly Lys Gly Val Pro Gly Lys Gly Val Pro Gly Lys Gly Val
        115                 120                 125

Pro Gly Lys Gly Val Pro Gly Lys Gly Val Pro Gly Lys Gly Val Pro
    130                 135                 140

Gly Lys Gly Val Pro Gly Lys Gly Val Pro Gly Val Gly Val Pro Gly
145                 150                 155                 160

Lys Gly Val Pro Gly Lys Gly Val Pro Gly Lys Gly Val Pro Gly Lys
                165                 170                 175

Gly Val Pro Gly Lys Gly Val Pro Gly Lys Gly Val Pro Gly Lys Gly
            180                 185                 190

Val Pro Gly Lys Gly Val Pro Gly Lys Gly Val Pro Gly Trp Pro His
        195                 200                 205

His His His His His
    210

<210> SEQ ID NO 15
<211> LENGTH: 413
<212> TYPE: PRT
<213> ORGANISM: Artificial Sequence
<220> FEATURE:
<223> OTHER INFORMATION: K72

<400> SEQUENCE: 15

Gly Ala Gly Pro Gly Val Gly Val Pro Gly Lys Gly Val Pro Gly Lys
1               5                   10                  15

Gly Val Pro Gly Lys Gly Val Pro Gly Lys Gly Val Pro Gly Lys Gly
            20                  25                  30

Val Pro Gly Lys Gly Val Pro Gly Lys Gly Val Pro Gly Lys Gly Val
        35                  40                  45

Pro Gly Lys Gly Val Pro Gly Val Gly Val Pro Gly Lys Gly Val Pro
    50                  55                  60

Gly Lys Gly Val Pro Gly Lys Gly Val Pro Gly Lys Gly Val Pro Gly
65                  70                  75                  80

Lys Gly Val Pro Gly Lys Gly Val Pro Gly Lys Gly Val Pro Gly Lys
                85                  90                  95

Gly Val Pro Gly Lys Gly Val Pro Gly Val Gly Val Pro Gly Lys Gly
            100                 105                 110

Val Pro Gly Lys Gly Val Pro Gly Lys Gly Val Pro Gly Lys Gly Val
        115                 120                 125

Pro Gly Lys Gly Val Pro Gly Lys Gly Val Pro Gly Lys Gly Val Pro
    130                 135                 140

Gly Lys Gly Val Pro Gly Lys Gly Val Pro Gly Val Gly Val Pro Gly
145                 150                 155                 160

Lys Gly Val Pro Gly Lys Gly Val Pro Gly Lys Gly Val Pro Gly Lys
                165                 170                 175

```
Gly Val Pro Gly Lys Gly Val Pro Gly Lys Gly Val Pro Gly Lys Gly
            180                 185                 190

Val Pro Gly Lys Gly Val Pro Gly Lys Gly Val Pro Gly Val Gly Val
            195                 200                 205

Pro Gly Lys Gly Val Pro Gly Lys Gly Val Pro Gly Lys Gly Val Pro
    210                 215                 220

Gly Lys Gly Val Pro Gly Lys Gly Val Pro Gly Lys Gly Val Pro Gly
225                 230                 235                 240

Lys Gly Val Pro Gly Lys Gly Val Pro Gly Lys Gly Val Pro Gly Val
                245                 250                 255

Gly Val Pro Gly Lys Gly Val Pro Gly Lys Gly Val Pro Gly Lys Gly
            260                 265                 270

Val Pro Gly Lys Gly Val Pro Gly Lys Gly Val Pro Gly Lys Gly Val
            275                 280                 285

Pro Gly Lys Gly Val Pro Gly Lys Gly Val Pro Gly Lys Gly Val Pro
    290                 295                 300

Gly Val Gly Val Pro Gly Lys Gly Val Pro Gly Lys Gly Val Pro Gly
305                 310                 315                 320

Lys Gly Val Pro Gly Lys Gly Val Pro Gly Lys Gly Val Pro Gly Lys
                325                 330                 335

Gly Val Pro Gly Lys Gly Val Pro Gly Lys Gly Val Pro Gly Lys Gly
            340                 345                 350

Val Pro Gly Val Gly Val Pro Gly Lys Gly Val Pro Gly Lys Gly Val
            355                 360                 365

Pro Gly Lys Gly Val Pro Gly Lys Gly Val Pro Gly Lys Gly Val Pro
    370                 375                 380

Gly Lys Gly Val Pro Gly Lys Gly Val Pro Gly Lys Gly Val Pro Gly
385                 390                 395                 400

Lys Gly Val Pro Gly Trp Pro His His His His His His
                405                 410
```